United States Patent [19]

Jacobs

[11] Patent Number: 5,010,473
[45] Date of Patent: Apr. 23, 1991

[54] METHOD AND APPARATUS FOR MODEL-BASED CONTROL OF AN OPEN-LOOP PROCESS

[75] Inventor: James R. Jacobs, Durham, N.C.

[73] Assignee: Duke University, Durham, N.C.

[21] Appl. No.: 401,996

[22] Filed: Aug. 31, 1989

[51] Int. Cl.$^5$ ............................ G05B 13/04; A61M 5/172
[52] U.S. Cl. ........................................ 364/150; 364/153; 604/65
[58] Field of Search ............... 364/148, 149, 150, 153; 604/151, 891, 51, 66, 31, 890.1, 65; 128/734

[56] References Cited

U.S. PATENT DOCUMENTS

| | | | |
|---|---|---|---|
| 4,280,494 | 7/1981 | Cosgrove, Jr. et al. | 128/213 R |
| 4,533,346 | 8/1985 | Cosgrove, Jr. et al. | 604/66 |
| 4,741,732 | 5/1988 | Crankshaw et al. | 604/50 |
| 4,810,243 | 3/1989 | Howson | 604/31 |
| 4,880,014 | 11/1989 | Zarowitz et al. | 128/734 |

*Primary Examiner*—Jerry Smith
*Assistant Examiner*—Paul Gordon
*Attorney, Agent, or Firm*—Christensen, O'Connor, Johnson & Kindness

[57] ABSTRACT

A method and apparatus for controlling a model based open-loop process and more specifically, the concentration of a drug delivered intravenously to a patient as a function of the rate of infusion. A three-compartment pharmacokinetic model is preferably used to determine the plasma drug concentrations corresponding to two arbitrarily selected rates of infusion. Based upon the linear relationship between corresponding data pairs, each pair comprising a rate of infusion and a corresponding plasma drug concentration, an interpolated rate is determined by a microprocessor (100) as a function of a specified plasma drug concentration, in accordance with program steps stored in a read only memory (ROM) 104. The actual infusion rate of the drug during successive time intervals is repetitively used to compute the plasma drug concentration at the end of each time interval. In each successive iteration, state variables from the previous computation of the plasma drug concentration are used to determine the next interpolated infusion rate. Any interruptions in the output from an infusion device (112) and variations from the interpolated value of the infusion rate are compensated. Using this open-loop control method and apparatus, the specified plasma drug concentration is rapidly achieved.

22 Claims, 7 Drawing Sheets

$$C_1(s) = \frac{k_0(s)V_1^{-1}(s+k_{21})(s+k_{31}) + C_1's^2 + [C_1'k_{31} + C_1'k_{21} + C_2'k_{21} + C_3'k_{31}]s + [C_1' + C_2' + C_3']k_{21}k_{31}}{s^3 + s^2(k_{10} + k_{12} + k_{21} + k_{13} + k_{31}) + s(k_{31}k_{21} + k_{10}k_{31} + k_{12}k_{31} + k_{13}k_{21}) + k_{10}k_{21}k_{31}}$$

FIG. 7.

$$C_1(t) = -\text{Rate}\,\frac{k_{21}k_{31}}{V_1 s_1 s_2 s_3}$$

$$+ \text{Rate}\left\{\left[\frac{k_{21}k_{31} + (k_{21}+k_{31})s_1 + s_1^2}{V_1 s_1(s_1-s_2)(s_1-s_3)} + \frac{C_1's_1^2 + [C_1'k_{21} + C_1'k_{31} + C_2'k_{21} + C_3'k_{31}]s_1 + [C_1' + C_2' + C_3']k_{21}k_{31}}{(s_1-s_2)(s_1-s_3)}\right]e^{s_1(t-t_0)}\right.$$

$$+ \left[\frac{k_{21}k_{31} + (k_{21}+k_{31})s_2 + s_2^2}{V_1 s_2(s_2-s_3)(s_2-s_3)} + \frac{C_1's_2^2 + [C_1'k_{21} + C_1'k_{31} + C_2'k_{21} + C_3'k_{31}]s_2 + [C_1' + C_2' + C_3']k_{21}k_{31}}{(s_2-s_1)(s_2-s_3)}\right]e^{s_2(t-t_0)}$$

$$+ \left.\left[\frac{k_{21}k_{31} + (k_{21}+k_{31})s_3 + s_3^2}{V_1 s_3(s_3-s_1)(s_3-s_2)} + \frac{C_1's_3^2 + [C_1'k_{21} + C_1'k_{31} + C_2'k_{21} + C_3'k_{31}]s_3 + [C_1' + C_2' + C_3']k_{21}k_{31}}{(s_3-s_1)(s_3-s_2)}\right]e^{s_3(t-t_0)}\right\}$$

FIG. 8.

$$C_3(t) = -\text{Rate}\frac{k_{13}k_{21}}{V_1 s_1 s_2 s_3}$$

$$+ \left\{ \text{Rate}\left[\frac{k_{13}(s_1+k_{21})}{V_1 s_1 (s_1-s_2)(s_1-s_3)} + \frac{C_1' s_1^2 k_{13} + [C_1' k_{21} + C_1' k_{31} + C_2' k_{21} + C_3' k_{31}]s_1 k_{13} + [C_1'+C_2'+C_3']k_{21}k_{31}k_{13}}{(s_1+k_{31})(s_1-s_2)(s_1-s_3)}\right] e^{s_1(t-t_0)} \right.$$

$$+ \left\{ \text{Rate}\left[\frac{k_{13}(s_2+k_{21})}{V_1 s_2 (s_2-s_1)(s_2-s_3)} + \frac{C_1' s_2^2 k_{13} + [C_1' k_{21} + C_1' k_{31} + C_2' k_{21} + C_3' k_{31}]s_2 k_{13} + [C_1'+C_2'+C_3']k_{21}k_{31}k_{13}}{(s_2+k_{31})(s_2-s_1)(s_2-s_3)}\right] e^{s_2(t-t_0)} \right.$$

$$+ \left\{ \text{Rate}\left[\frac{k_{13}(s_3+k_{21})}{V_1 s_3 (s_3-s_1)(s_3-s_2)} + \frac{C_1' s_3^2 k_{13} + [C_1' k_{21} + C_1' k_{31} + C_2' k_{21} + C_3' k_{31}]s_3 k_{13} + [C_1'+C_2'+C_3']k_{21}k_{31}k_{13}}{(s_3+k_{31})(s_3-s_1)(s_3-s_2)}\right] e^{s_3(t-t_0)} \right.$$

$$+ \left\{ C_3' + \frac{C_1' k_{31}^2 k_{13} - [C_1' k_{21} + C_1' k_{31} + C_2' k_{21} + C_3' k_{31}]k_{31} k_{13} + [C_1'+C_2'+C_3']k_{21}k_{31}k_{13}}{(-k_{31}-s_1)(-k_{31}-s_2)(-k_{31}-s_3)}\right\} e^{-k_{31}(t-t_0)}$$

FIG. 9.

$$C_2(t) = -\text{Rate}\frac{k_{12}k_{31}}{V_1 s_1 s_2 s_3}$$

$$+ \underbrace{\text{Rate}\left[\frac{k_{12}(s_1+k_{31})}{V_1 s_1(s_1-s_2)(s_1-s_3)}\right] + \frac{C_1' s_1^2 k_{12} + [C_1' k_{21} + C_1' k_{31} + C_2' k_{21} + C_3' k_{31}]s_1 k_{12} + [C_1' + C_2' + C_3']k_{21}k_{31}k_{12}}{(s_1+k_{21})(s_1-s_2)(s_1-s_3)}}_{e^{s_1(t-t_0)}}$$

$$+ \underbrace{\text{Rate}\left[\frac{k_{12}(s_2+k_{31})}{V_1 s_2(s_2-s_1)(s_2-s_3)}\right] + \frac{C_1' s_2^2 k_{12} + [C_1' k_{21} + C_1' k_{31} + C_2' k_{21} + C_3' k_{31}]s_2 k_{12} + [C_1' + C_2' + C_3']k_{21}k_{31}k_{12}}{(s_2+k_{21})(s_2-s_1)(s_2-s_3)}}_{e^{s_2(t-t_0)}}$$

$$+ \underbrace{\text{Rate}\left[\frac{k_{12}(s_3+k_{31})}{V_1 s_3(s_3-s_1)(s_3-s_2)}\right] + \frac{C_1' s_3^2 k_{12} + [C_1' k_{21} + C_1' k_{31} + C_2' k_{21} + C_3' k_{31}]s_3 k_{12} + [C_1' + C_2' + C_3']k_{21}k_{31}k_{12}}{(s_3+k_{21})(s_3-s_1)(s_3-s_2)}}_{e^{s_3(t-t_0)}}$$

$$+ \underbrace{C_2' + \frac{C_1' k_{21}^2 k_{12} - [C_1' k_{21} + C_1' k_{31} + C_2' k_{21} + C_3' k_{31}]k_{21} k_{12} + [C_1' + C_2' + C_3']k_{21}k_{31}k_{12}}{(-k_{21}-s_1)(-k_{21}-s_2)(-k_{21}-s_3)}}_{e^{-k_{21}(t-t_0)}}$$

*FIG. 10.*

METHOD AND APPARATUS FOR MODEL-BASED CONTROL OF AN OPEN-LOOP PROCESS

TECHNICAL FIELD

This invention generally pertains to a model-driven method and apparatus for controlling an open-loop process, and specifically, to controlling the rate at which a drug is administered to a recipient to achieve a specified plasma drug concentration.

BACKGROUND OF THE INVENTION

Most process control schemes are closed-loop, depending upon a feedback signal that either directly or indirectly indicates the effect on the process output of changes in the output of one or more actuators. In an open-loop control process, a feedback signal is normally not available, typically because the output of the process is difficult, expensive, or impossible to monitor in a timely fashion. Open-loop processes are sometimes automatically controlled by using a model to predict the process output as a function of the output from the controlled actuator. The accuracy with which the process is controlled then depends simply on how accurately the model reflects the actual behavior of the process.

For example, a physician using an infusion device (actuator) to administer a drug intravenously to a patient may program an infusion device controller to achieve user-specified plasma drug concentrations based on a pharmacokinetic model of the drug being infused. The infusion device controller uses the pharmacokinetic model to dynamically determine the drug delivery rate at which the infusion device should be operated to achieve the specified plasma drug concentration. The infusion device infuses drug to the recipient, and the drug becomes present within the plasma of the recipient at some concentration. Ideally, the ability of the infusion device controller and the infusion device to achieve the specified plasma drug concentration would depend on the accuracy and applicability of the pharmacokinetic model. However, most drug infusion devices have a limited range of delivery rates, and a limited resolution for specifying or controlling the delivery rate. If the control method computes a delivery rate that is outside the available range of delivery rates and/or the actual delivery rate does not equal the computed rate due to lack of resolution of the infusion device, a significant difference between the theoretical and actual plasma drug concentrations may develop over time. Furthermore, if, for example, sensors within the infusion device detect an occlusion of the catheter line connecting the infusion device to the recipient and cause the infusion device to halt drug delivery, the theoretical and actual plasma drug concentrations may diverge unless the controller and pharmacokinetic simulation are advised of the interruption in drug delivery and compensate accordingly once drug delivery is resumed. Thus, in a model-based control method, the model simulation must be apprised of the actual output of the actuator (input to the process), not the desired output of the actuator.

SUMMARY OF THE INVENTION

In accordance with the present invention, a method and apparatus are provided for controlling a process to obtain a specified output, $O_s$, where the process is described by a model that defines an output of the process as a function of a specified control signal. The first step in the method provides for arbitrarily selecting a first value, $X_1$, and a second value, $X_2$, for the control signal, and initializing a plurality of state variables in the model. First and second output values, $O_1$ and $O_2$, that would be obtained at the end of a time interval, $\Delta t$, were the control signal to be applied for this time, are then determined as a function of the first and second values of the control parameter using the model. Assuming that a linear relationship exists between data pairs ($O_1$, $X_1$) and ($O_2$, $X_2$), the method interpolates with respect to these data pairs, to determine a desired value, $X_d$, for the control signal that should produce the specified output.

During the time interval, the process is operated nominally using the desired value, $X_d$, for the control signal. While the process is being operated, a value, $X_a$, of the control signal actually used in the process is determined. Using the model, a computed value for the process output, $O_c$, is determined as a function of the value, $X_a$, of the control signal. Each of these steps is reiteratively repeated, each successive iteration using values for state variables in the model that depend on the computed value of the process output determined in a previous iteration. As a result, the actual process output is tracked, causing the process to quickly converge on the specified output.

The step of interpolating includes the steps of determining the difference between the second and first control signals, $X_2 - X_1$, and the difference between the second and first corresponding output values, $O_2 - O_1$. Thereafter, the slope of a line through the data pair ($O_1$, $X_1$) and the data pair ($O_2$, $X_2$) is determined from the relationship:

$$\text{slope} = (O_2 - O_1)/(X_2 - X_1).$$

The desired control parameter, $X_d$, is then determined from the relationship:

$$X_d = (O_s - (O_1 - \text{slope} * X_1))/\text{slope}.$$

In a case where the process includes constraints on the values of the control signal that can be used in the process, the step of operating the process for the time interval includes the step of using a value for the control signal that approximates the desired value of the control signal as closely as the constraints allow. As an example, the constraints may comprise limits on the maximum and/or minimum values of the control signal. Alternatively, the constraints may comprise limits on the resolution of the values of the control signal usable in the process.

If the actual control signal substantially equals zero for one or more of the time intervals due to a process fault, the step of determining the control signal, $X_a$, actually implemented in the process includes the step of computing a change in the output during a total accumulated time that the process fault continues. As a result, upon correction of the process fault, the step of determining the desired value of the control parameter compensates for the total accumulated time in which the process was not operated with the desired control signal.

More specifically, the method may relate to controlling the concentration of a drug administered intravenously at a controlled rate to a recipient to achieve a specified plasma drug concentration, wherein a linear pharmacokinetic model is used that predicts the plasma drug concentration as a function of the rate the drug is administered and as a function of a plurality of state variables and other parameters that define the current concentration of the drug in the recipient's body. Analogous steps in practicing this method are included as a further aspect of the invention. Apparatus including a plurality of means for carrying out the functions defined as steps in the above method comprise a further aspect of the invention.

DESCRIPTION OF THE PREFERRED EMBODIMENTS

Although the present invention was developed specifically for controlling the rate of intravenous infusion of a drug to achieve a specified plasma drug concentration, it must be emphasized that the invention has general application to any model-based control paradigm where the relationship between time, the output of the controlled actuator (input to the process), and the output of the process are described by a linear dynamic model. Details of the particular model used to calculate the output of the process as a function of the actuator output are not important to the present invention. However, the accuracy with which the specified process output is obtained does depend upon the quality of the model used. To emphasize this point, FIG. 1 includes a block diagram that schematically defines how such an open-loop process is controlled to achieve the specified output using a model-based control paradigm. It is presumed that the value of the actual output of the process is either difficult or impossible to measure in a timely fashion, or is otherwise not available as feedback signal for use in a conventional, real-time, closed-loop control of the process.

Figure 1:
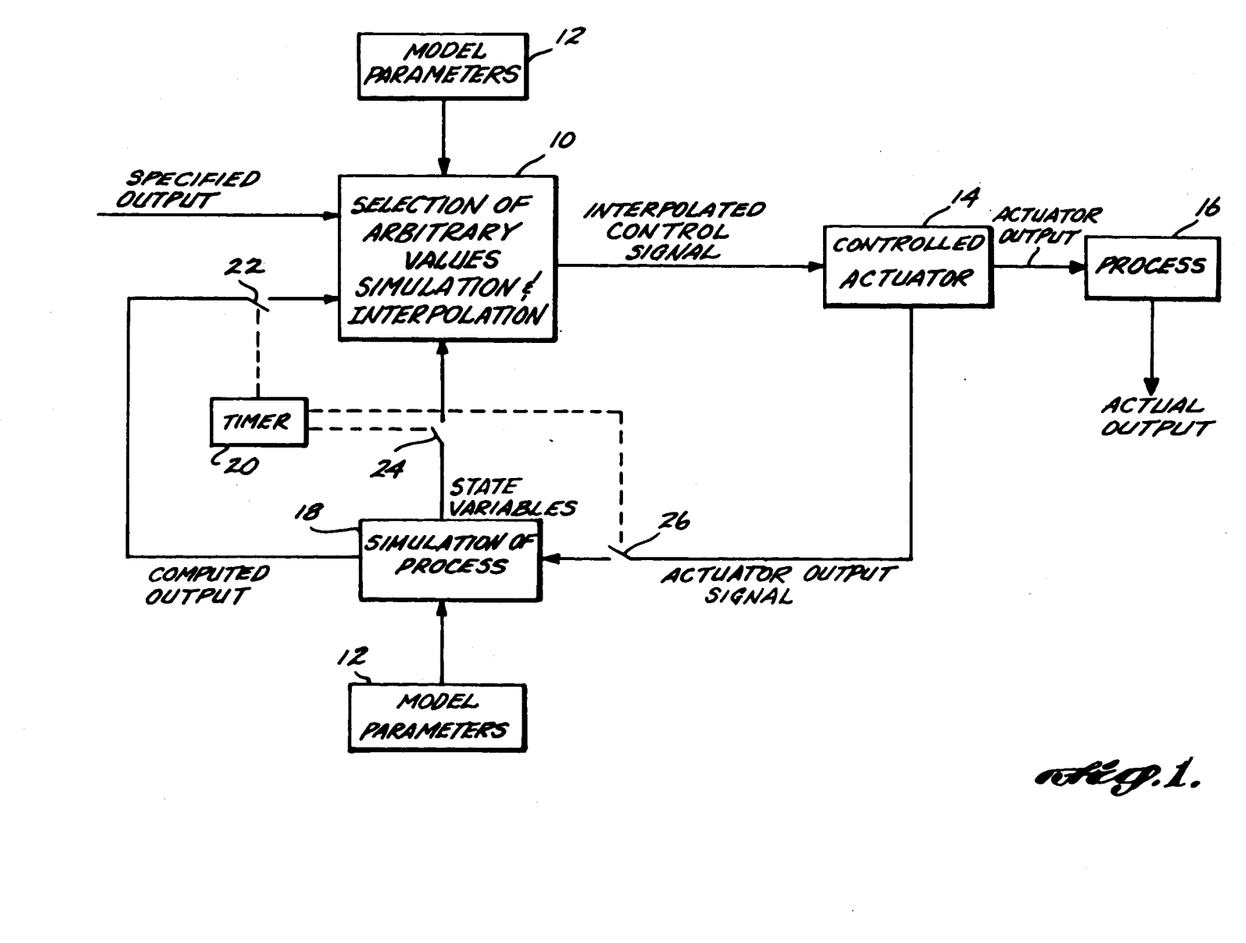
FIG. 1 is a block diagram illustrating the steps implemented in model-based control of an open-loop process to achieve a specified output.

As shown in FIG. 1, a value for the specified output of the process is input to a block 10. In block 10, a first and a second value for the actuator output, which nominally determine the output of the process, are arbitrarily selected. These first and second values must not be equal to each other and should preferably be within a range relevant to the control process, but are otherwise entirely arbitrary. A block 12 includes parameters and constants of equations that model and simulate the process to be controlled as a function of an actuator output and as a function of time intervals, $\Delta t$. With the model state variables initialized to their state at the end of the most recent time interval, $\Delta t_{n-1}$, a first arbitrarily selected value for the actuator output (input to process) to be used during $\Delta t_n$ is used as an input to the model to calculate the output value that would be obtained at the end of $\Delta t_n$. With the model similarly initialized, a second arbitrary selected value for the actuator output (input to process) to be used during $\Delta t_n$ is used as an input to the model to calculate the output value that would be obtained at the end of $\Delta t_n$.

Since the model responds linearly to changes in input, a linear relationship exists with respect to data pairs that each include one of the arbitrarily selected first and second values for the actuator output and the computed value for the output of the process corresponding to that value for the period $\Delta t_n$. Because of this linear relationship, it is possible to interpolate along a line extending through these two data pairs to determine an interpolated actuator control signal that should nominally be used during the next time interval to achieve or maintain the specified process output.

The interpolated signal is provided to a block 14 for controlling an actuator to modify the output of the process. This relationship is indicated by the arrow connecting block 14 to a block 16. Block 16 is labeled Process, and generally represents the plant or other mechanism in which the process is effected. The "actual output" developed by the process in block 16 represents a quantity that would normally be used as a feedback signal for closed-loop control of the process, if this output could readily be measured in a timely fashion.

If the actuator is able to respond precisely to the interpolated control signal, the actual output from block 16 should equal the desired process output by the end of the first sampling interval, at least within the accuracy limits of the model. However, if the interpolated control signal is outside of the actuator's range, or if the actuator cannot respond with as much resolution as the control signal specifies, or if the actuator is nonfunctional for some portion of the time interval, then the actual process output will differ from that specified.

The present invention compensates for the failure of the actuator to use the interpolated control signal determined in block 10 exactly by using a signal indicative of the actual output of the actuator. This signal is input to a block 18. In block 18, the model parameters and equations from block 12 are used to determine a computed process output that corresponds to the actual actuator output used in controlling the process in block 16 and the actual duration of the sampling interval. The computed output of the process may differ from the specified output due to a failure in the actuator, lack of resolution or precision in the ability of the actuator to use the interpolated control signal, or because the interpolated control signal lies outside the available range of the actuator. Since the state variables in the model used to derive the interpolated control signal are computed from the actual performance of the actuator, not the desired performance of the actuator, the interpolated control signal is inherently and always that which is optimally suited to achieve the desired process output during the next sampling interval.

At the end of each sampling interval, determined by a timer in a block 20, a switch 22 is closed and the computed output from block 18 is input to block 10. At the same time, a plurality of state variables developed in the equations that define the model as a function of the actual actuator output used as the input to the simulation of the process in block 18 are input to block 10 through a switch 24. This switch is also controlled by the timer in block 20. The timer in block 20 may operate at regular predefined intervals or may also be interrupt- or event-driven.

In block 10, at the end of each preceding sampling interval, the arbitrarily selected first and second values for the actuator output are respectively input to the model to calculate corresponding first and second simulated process output values, and a new interpolated control signal is determined based on the liner relationship between the resulting data pairs and the specified process output value. Each successive time that a new interpolated control signal is thus determined (for a period $\Delta t_n$), the model is first updated with the state variables from the previous iteration (for the preceding period $\Delta t_{n-1}$), which are provided from block 18 and which depend upon the actual actuator output used during the previous interval of time ($\Delta t_{n-1}$). Using this method, the actual output of the process approaches the specified output and tracks interruptions or variations in the operation of the actuator.

Figure 2:
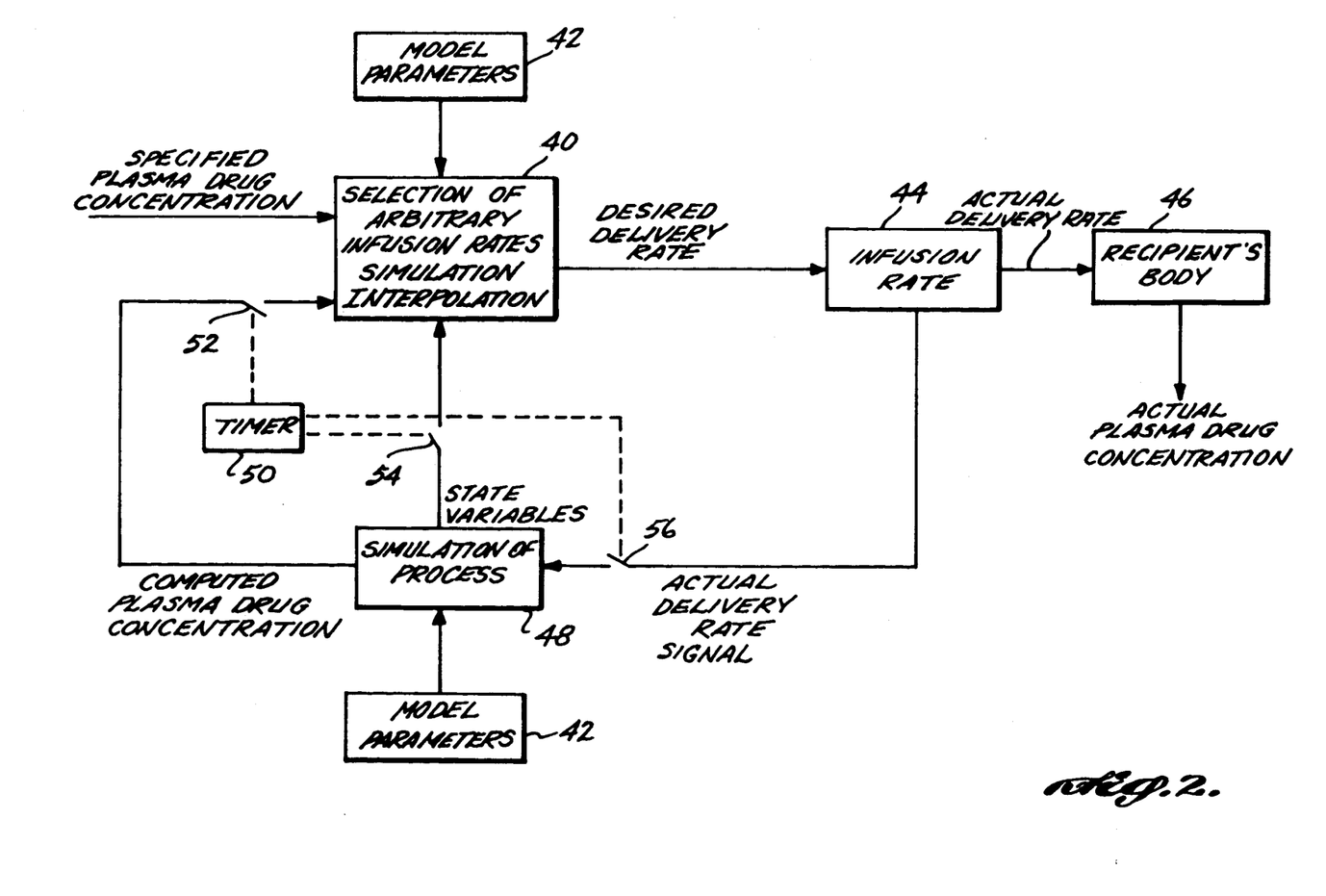
FIG. 2 is a block diagram showing the steps of the method in the present invention as applied to obtaining a specific plasma concentration of a drug administered by intravenous infusion, wherein the actuator is an infusion device having a controlled delivery rate for infusing the drug into a recipient.
Figure 4:
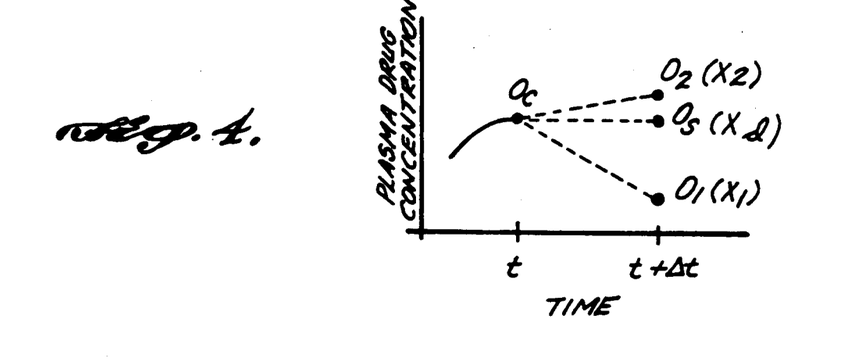
FIG. 4 is a graph illustrating the plasma concentration of a drug at a time, t, in respect to the plasma drug concentrations corresponding to two arbitrary delivery rates, at a time, $t + \Delta t$.

Turning now to FIG. 2, the specific application of the present invention to obtaining a specified plasma concentration of a drug administered intravenously is illustrated in a schematic block diagram, similar to that of FIG. 1. The desired plasma drug concentration is input to a block 40. Note that in this disclosure, the word "plasma" may be used interchangeably with words suggesting other constituents of blood (e.g., whole blood, serum, free fraction), depending on the particular implementation and application. Arbitrary infusion rates are selected and used as separate inputs to a linear pharmacokinetic model for the drug for calculation of two corresponding plasma drug concentrations that would be obtained if the selected infusion rates were to be utilized during the next time interval. Based upon the linear relationship between corresponding data pairs comprising the first and second arbitrarily selected infusion rates and the corresponding plasma drug concentrations, a desired infusion rate for the drug is determined by interpolation with respect to the desired plasma drug concentration. Details of the interpolation process are graphically illustrated in FIGS. 4 and 5.

Figure 5:
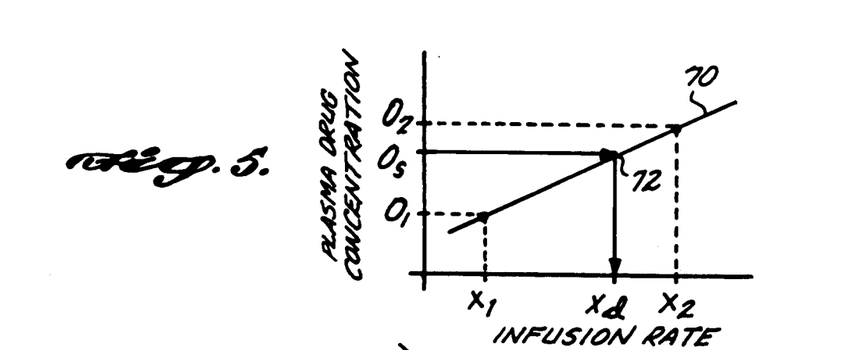
FIG. 5 is a graph illustrating an interpolation step used to compute a desired rate of infusion to achieve the specified plasma drug concentration.

With the pharmacokinetic model initialized to its state at the end of the previous infusion interval, $\Delta t_{n-1}$, a first arbitrarily selected infusion rate $X_1$ is input to the model defined by parameters provided from a block 42. Using the model, a first plasma drug concentration, $O_1$, that would result at the end of the impending infusion interval, $\Delta t_n$, if the drug at the first arbitrarily selected infusion rate $X_1$ were to be delivered by the infusion device for the internal $\Delta t_n$ is determined. Similarly, a second plasma drug concentration, $O_2$, that would result at the end of the impending infusion interval, $\Delta t_n$, if the drug at a second arbitrarily selected infusion rate $X_2$ (different than $X_1$) were to be delivered by the infusion device for the interval $\Delta t_n$, is determined. A line 70 in FIG. 5 is drawn through the data pairs ($X_1$, $O_1$) and ($X_2$, $O_2$). A specified plasma drug concentration, $O_s$, defines a point at a reference numeral 72 on line 70. A vertical line dropped from point 72 intercepts a corresponding infusion rate at $X_d$. Thus, the interpolated infusion rate, $X_d$, is the desired ideal infusion rate that should be used during the infusion interval $\Delta t_n$ as an input to a block 44 to control the infusion device for infusing drug into the recipient. All of these calculations are made during a time much, much smaller than $\Delta t_n$ so that they can be considered to have been performed substantially instantaneously during the time between the end of $\Delta t_{n-1}$ and the start of $\Delta t_n$, even though $\Delta t_{n-1}$ and $\Delta t_n$ are stepwise continuous in time. The infusion of the drug into the recipient's body is represented by the line connecting block 44 to a block 46. Block 46 is labeled Recipient's Body, but in a larger sense indicates the pharmacological process that determine the actual plasma drug concentration. A recipient's body weight, sex, age, and many other factors may affect the actual plasma drug concentration resulting from a particular drug dosage, and some of these factors may be embodied in the model parameters provided in a block 42. The only variable controlled to achieve the specified plasma drug concentration is the rate at which the drug is infused into the recipient by the infusion device in block 44.

Although determined graphically in FIG. 5, the interpolated delivery rate input to the infusion device in block 44 may also be interpolated mathematically from the corresponding data pairs ($X_1$, $O_1$) and ($X_2$, $O_2$) and specified plasma concentration of the drug based on the relationship:

$$X_d = (O_s - (O_1 - b \cdot X_1))/b \qquad (1)$$

where $b = (O_2 - O_1)/(X_2 - X_1) = $ slope of the line through ($X_1$, $O_1$) and ($X_2$, $O_2$).

For the purposes of this disclosure and the claims that follow, the term "interpolation" is intended to encompass both graphical and numeric methods of determining the interpolated control signal or ideal drug infusion rate.

The interpolation control signal or ideal drug infusion rate may not be achieved if the infusion device in block 44 can only be set to deliver the drug, for example, at integer values of an infusion rate. Furthermore, the interpolated or desired ideal infusion rate may exceed the maximum infusion rate at which the infusion device in block 44 can deliver the drug into the recipient's body, and of course the infusion device cannot remove drug from the recipient (negative infusion rate). Also, an occlusion of the catheter line connecting the infusion device to the recipient's body, or a fault in the infusion device such as mechanical breakdown, may interrupt drug delivery to the recipient. For these and other reasons, the infusion device may infuse the drug at an actual infusion rate that differs from the desired rate. The present invention compensates for these limitations. A signal indicative of the actual infusion rate is provided from block 44 to a block 48. In block 48, the actual infusion rate is input to the model to compute a plasma concentration of the drug that corresponds to the actual rate of infusion of drug into the recipient. This "actual" infusion rate is typically not a measured infusion rate but rather is the infusion rate nominally reported by the infusion device, which results from the electronic and/or mechanical properties of the infusion device in the given circumstances.

Block 42 contains the model parameters, constants, and equations that are used to define the simulation of the process in block 48 so that the theroretical plasma concentration can be computed. At the end of an infusion interval $\Delta t_n$, the timer in a block 50 closes a switch 56 so that a signal indicative of the actual infusion rate generated by the infusion device during $\Delta t_n$ is input to a block 48. At the end of an infusion interval $\Delta t_n$, determined by a timer in block 50, a switch 52 is closed to provide the computed plasma concentration as an input to block 40. In addition, the timer in block 50 closes a switch 54 so that state variables corresponding to parameters in the model that change with each computation of a new computed plasma concentration are input to block 40. Also, after each predetermined time interval, block 40 again determines the desired infusion rate by interpolation between the data pairs comprising the arbitrarily selected first and second delivery rates and corresponding plasma concentrations that are determined each time from the model. As this iterative process proceeds, the actual plasma concentration in the recipient's body quickly approaches the specified plasma concentration input to block 40 (unless infusion of the drug is interrupted by an infusion device fault or an occlusion of a catheter line, for example).

Switches 52, 54, and 56 conveniently represent gated data transfer events and are not actual electrical switches. Typically, these switches will be gated at the end of each particular sampling interval $\Delta t_n$, but the timer in block 50 that gates these switches may be event- or interrupt-driven such that data transfer occurs at a time before the scheduled end of $\Delta t_n$. Examples of events that would ideally result in the premature termination of the current infusion period are when the microprocessor detects an error or fault condition altering the rate of drug delivery or when a new specified plasma drug concentration is entered by the user into block 40. In any case, the timer in block 50 determines the actual duration of each sampling interval and reports that interval to the simulation in block 48.

If a physician changes the value of the specified plasma concentration of the drug that is input to block 40, the ideal or desired infusion rate changes correspondingly. The state variables that are transferred through switch 54 from block 48 to block 40 and the computed value for plasma concentration that are used in each successive iteration compensate for the change in delivery rate to achieve the new specified plasma concentrations. As shown in FIG. 5, the value for the computed plasma concentration, $O_c$, at time t, forms a basis for computing the plasma concentration corresponding to the arbitrarily selected rates of infusion $X_1$ and $X_2$, at time $t+\Delta t$. In the preferred embodiment, the timer in block 20 normally closes switches 52, 54, and 56 at nine-second intervals, i.e., $\Delta t = 9$ seconds, unless interrupted prior to the end of that time. Due to the relatively short time interval between iterations, the control method readily tracks changes in the desired plasma concentration input by medical personnel.

Figure 3:
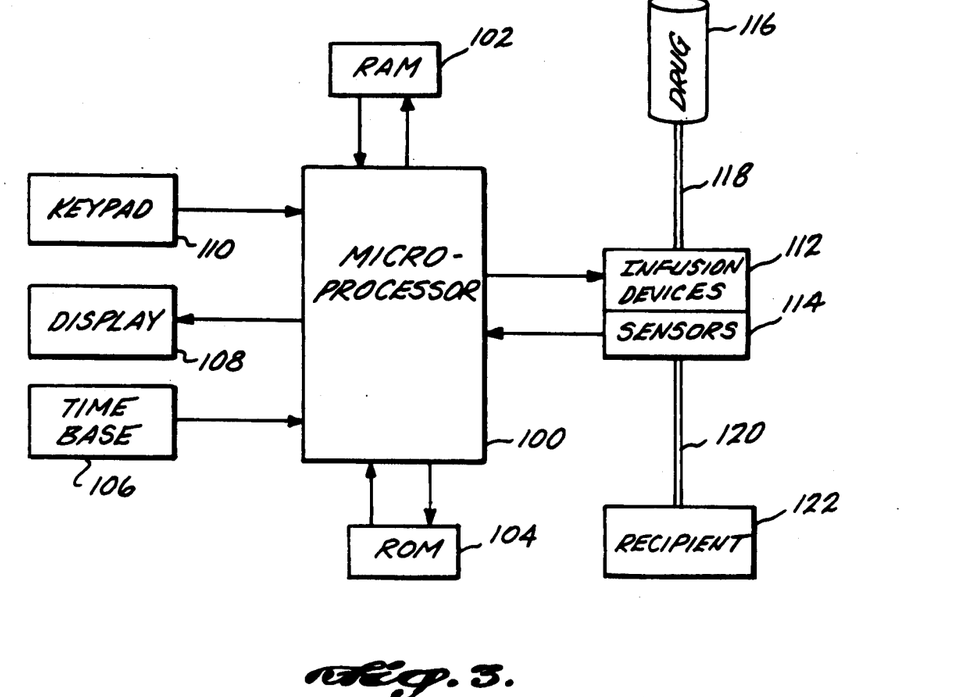
FIG. 3 is a block diagram of a microprocessor control for a drug infusion device.

Referring to FIG. 3, a control that implements the above-described method comprising one aspect of the present invention is illustrated in a block diagram. The control includes a microprocessor 100, which is connected to a random access memory (RAM) 102 in which data is temporarily stored, and to a read-only memory (ROM) 104 in which are defined program steps implemented by the microprocessor for controlling the infusion device to deliver a drug to a patient. A time base 106 is connected to microprocessor 100, and may comprise a crystal controlled oscillator or conventional RC circuit, as is well known to those of ordinary skill in the art. Using time base 106 as a time/frequency reference, microprocessor 100 determines the predetermined interval of time for each successive iteration in blocks 40 and 48. Also connected to microprocessor 100 are a display 108 and a keypad 110. In response to prompt messages made to appear on display 108, medical personnel enter data describing characteristics of the patient that are required by the model, the type of drug to be infused, and the desired plasma concentration of the drug. The prompt messages shown on display 108 comprise part of the program steps stored in ROM 104, and the data entered by the medical personnel are temporarily stored in RAM 102.

Microprocessor 100 controls an infusion device 112 to infuse the drug as described above. Although control of infusion device 112 involves many other considerations, for purposes of this disclosure, the primary control parameter effected in infusion device 112 by the microprocessor is the rate at which the infusion device delivers drug to the patient. Since the control including microprocessor 100 is integral with infusion device 112 in the preferred embodiment, the rate of infusion and resolution with which this parameter is achievable by the infusion device are stored in ROM 104 and are thus readily accessible by microprocessor 100. For example, infusion device 112 may have an operating range of infusion rates of between 10 and 999 ml per hour, specifiable only in integer values. Microprocessor 100 determines the actual infusion rate (at least in part) from such data.

A drug reservoir 116 is connected to supply the drug at the specific concentration to infusion device 112 through a supply line 118. The drug is typically infused intravenously into a recipient 122 through a catheter line 120. Infusion device 112 includes a plurality of sensors for detecting fault conditions that can prevent the infusion device from delivering the drug to a patient. For example, the sensors can detect an occlusion in catheter line 120, and other fault conditions. In response to any such fault condition, sensors 114 produce a binary signal indicating that the drug is not being delivered to recipient 122. As noted above, the actual infusion rate is determined by microprocessor 100, with respect to the operating specifications for infusion device 112 that are stored within ROM 104, and also with respect to one or more binary signals supplied to the microprocessor from sensors 114. Microprocessor 100 thus compensates for changes in the plasma drug concentration caused by any interruption of drug infusion, by using an actual infusion rate equal to zero during the simulation of the process in block 48 of FIG. 2 while the interruption continues. Once the fault is corrected and delivery of the drug to the recipient is resumed, a nonzero value for the actual delivery rate, which reflects the actual operating capabilities of the infusion device is again input to block 48 to determine the current value of computed plasma concentration of the drug, compensated for the period of time in which drug was not infused into the recipient.

Figure 6:
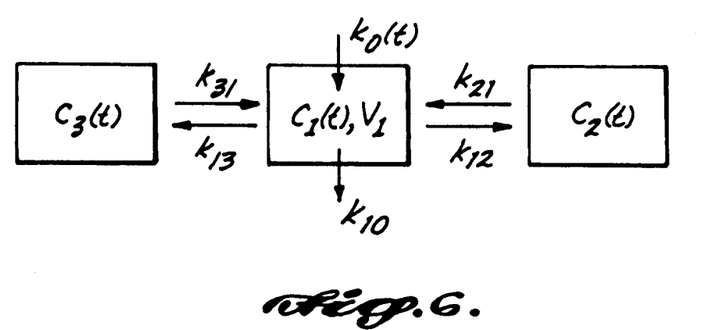
FIG. 6 is a schematic representation of a three-compartment pharmacokinetic model of drug assimilation in the body for use in determining the plasma concentration of the infused drug.

To better appreciate the advantages of the present invention in controlling the open-loop drug infusion process represented in FIG. 2, it is helpful to understand a specific model used for calculating the plasma concentration of a drug as a function of the rate at which the drug is infused into a recipient's body. For this purpose, a three-compartment, open pharmacokinetic model is illustrated in FIG. 6. In this model, the rate of drug infusion is represented by the variable $k_0(t)$ and the rate constant for drug elimination from the body by the constant $k_{10}$. The plasma drug concentration is identified by the variable $C_1(t)$. The apparent volume of the central or plasma compartment is $V_1$. The two other compartments in the model include drug concentrations identified respectively by the terms $C_2(t)$ and $C_3(t)$ and are hypothetical peripheral compartments in the body. One of the peripheral compartments, for example, may represent well perfused tissue and the other poorly perfused tissue. In the formulation given here, the volume of the peripheral compartments is assumed to be equal to $V_1$ also. Drug moves between the central compartment (the plasma) and one of the peripheral compartments bidirectionally with rate constants $k_{31}$ and $k_{13}$. Similarly, drug moves bidirectionally between the other peripheral compartment and the central compartment with rate constants $k_{21}$ and $k_{12}$. The data specifying the values for these constants that should be used for a particular drug and patient characteristics are stored in ROM 104 (FIG. 3). Using the model, the method described above is effected to control the infusion rate, $k_0(t)$, of the infusion device to achieve a value of $C_1(t)$ that equals the specified plasma drug concentration.

FIG. 6 is a pictorial abstraction of the following system of linear differential equations that define the three-compartment model:

$$dC_1(t)/dt = k_0(t)/V_1 - [k_{10} + k_{12} + k_{13}]C_1(t) + k_{21}C_2(t) + k_{31}C_3(t) \quad (2)$$

$$dC_2(t)/dt = k_{12}C_1(t) - k_{21}C_2(t) \quad (3)$$

$$dC_3(t)/dt = k_{13}C_1(t) - k_{31}C_3(t) \quad (4)$$

Figure 7:
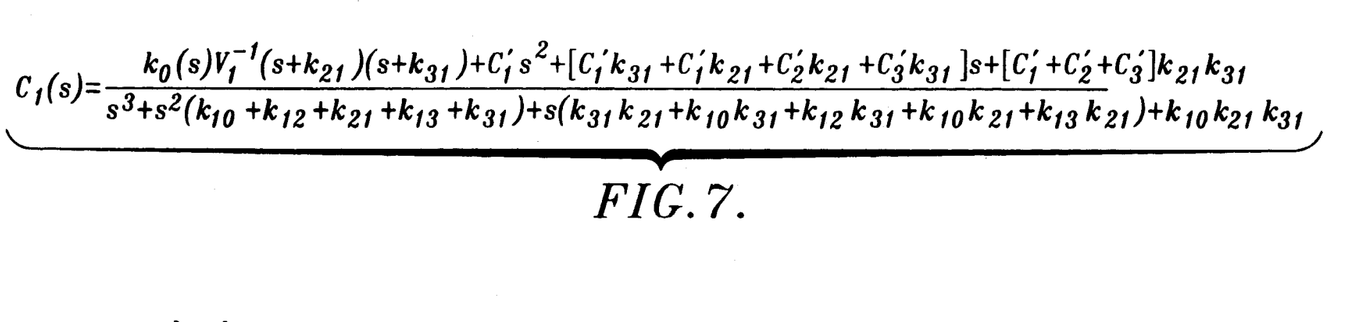
FIG. 7 is a transfer function defining the three-compartment model of drug disposition in the body.

The Laplace transform of each of Equations 2, 3, and 4 can be taken and the resulting simultaneous equations manipulated algebraically to form an equation (transfer function) 5, shown in FIG. 7, which relates the central compartment drug concentration, i.e., plasma drug concentration, to the rate of intravenous drug administration, i.e., $k_0(t)$.

Figure 8:
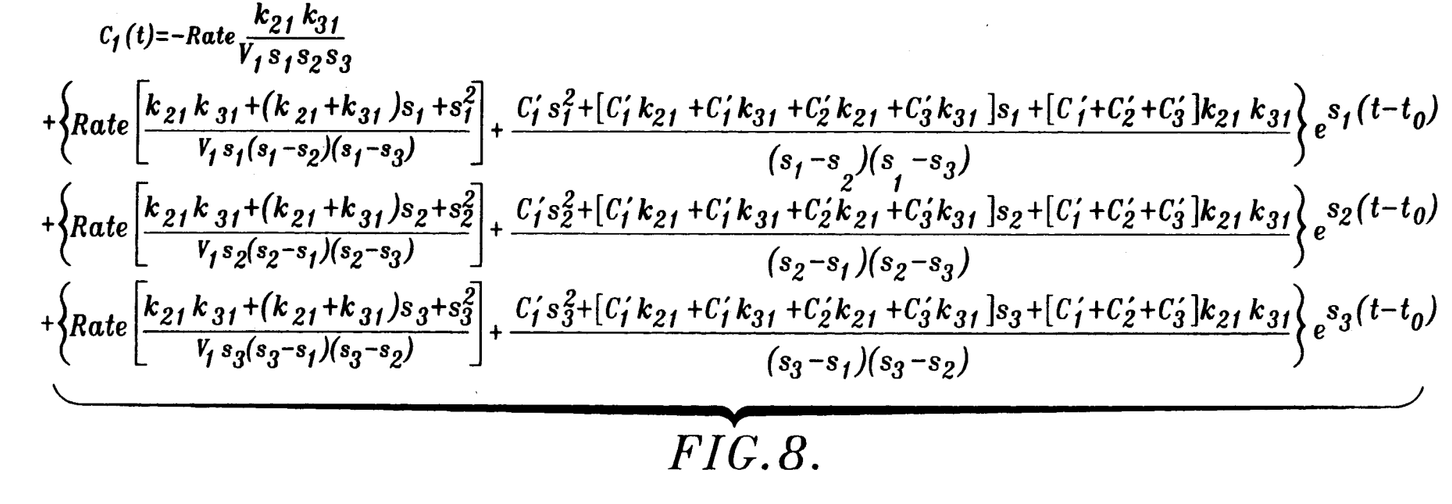
FIGS. 8–10 represent equations defining the concentration of the drug in each of the three compartments of the model of FIG. 6.
Figure 9:
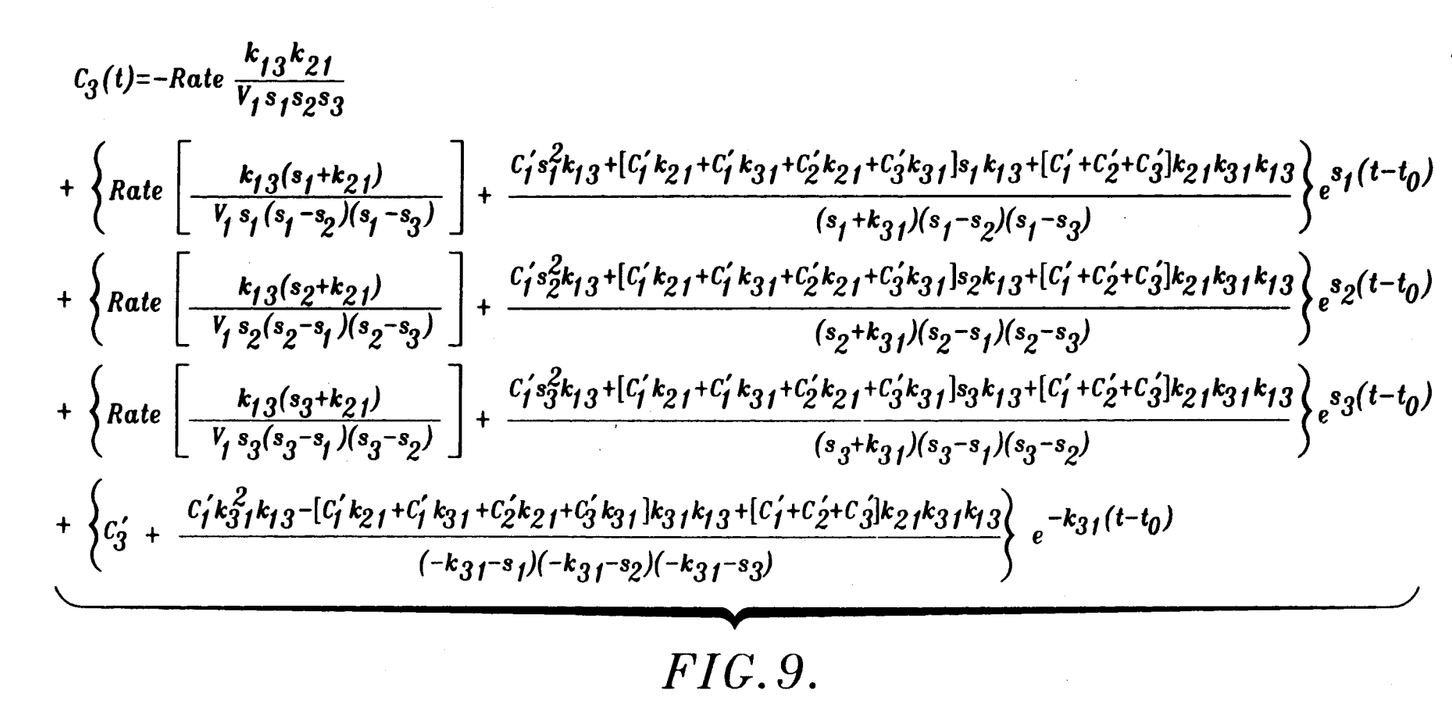
Figure 10:
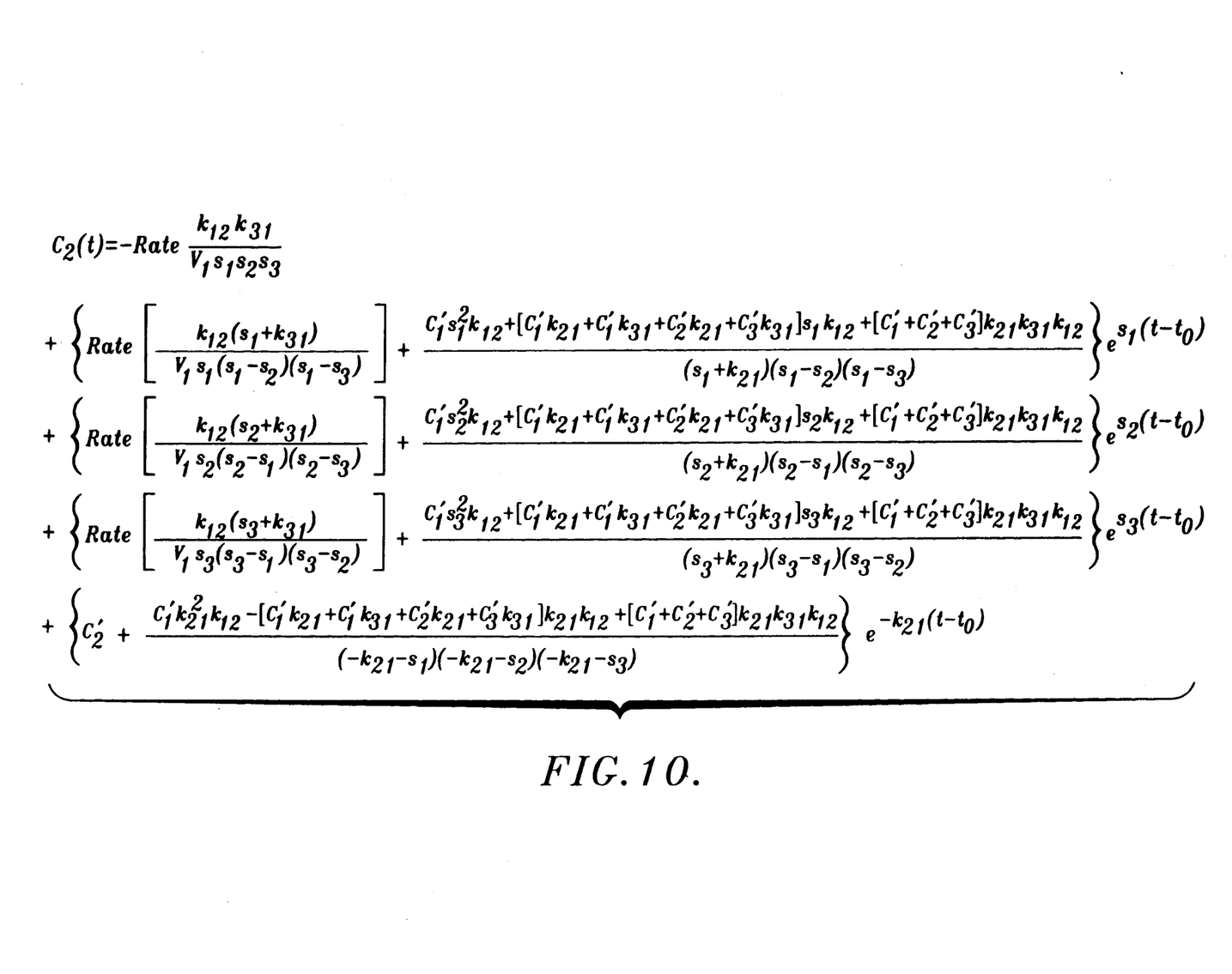

In Equation 5, FIG. 7, s is the Laplacian operator and the constants $k_{31}$, $k_{13}$, $k_{12}$, $k_{21}$, $k_{10}$, and $V_1$ are as illustrated in FIG. 6. The actual values of the rate constants and central compartment volume used depend upon the particular drug to which the model is applied and upon the characteristics of the recipient. From Equation 5, expressions for the concentration of the drug in each of the three compartments of the model are developed, as shown for Equations 6, 7, and 8 in FIGS. 8–10, respectively. Each of these expressions is relatively complex with respect to the number of terms involved, but is readily solved by microprocessor 100. The values $s_1$, $s_2$, and $s_3$ comprise the cubic roots of the denominator of Equation 5. $C'_i = 1, 2, 3$, represent the concentration in each of the respective compartments at the end of a particular infusion interval, $t - t_0$, where t is the current real or simulated time and $t_0$ is the real or simulated time at the end of the previous infusion interval, i.e., at the end of the previous $\Delta t$. Accordingly, at the end of each successive infusion interval, $C_1(t)$, $C_2(t)$, and $C_3(t)$ can be computed in Equations 6, 7, and 8. $C_1(t)$, $C_2(t)$, and $C_3(t)$ are the state variables in this system of equations and, along with the aforementioned constants, completely describe the system at any point in time.

Although the present invention is described with respect to use of a three-compartment model, it should be apparent that other models may be used to determine the drug infusion rates necessary to achieve a specified plasma drug concentration in a pharmacokinetic model-based infusion device. In a more general sense, it should be apparent that the present invention is applicable to virtually any automatic control paradigm in which the relationship between the output of the controlled actuator and the output of the process to be controlled is described by a linear dynamic model.

It will further be apparent that modifications may be made to the present invention within the scope of the claims that follow. Accordingly, the invention is not in any way intended to be limited by the disclosure of the preferred embodiments but is defined entirely by reference to the claims.

What is claimed is:

1. A method for controlling a process to obtain a specified output, $O_s$, where the process is described by a linear model that defines an output of the process as a function of a specified control signal, wherein the control signal controls an actuator that affects the process, said method comprising the steps of:

(a) arbitrarily selecting a first value, $X_1$, and a second value, $X_2$, for the control signal, and initializing a plurality of state variables in the model;

(b) as a function of the first and second values of the control signal, which are respectively input to the model, determining corresponding first and second output values, $O_1$ and $O_2$, that would be obtained at the end of an interval of time, $\Delta t$, were the control signal to be applied for this interval;

(c) interpolating with respect to the first and second values of the control signal and corresponding first and second output values to determine a desired value, $X_d$, for the control signal that should produce the specified output, $O_s$, at the end of the time interval, $\Delta t$;

(d) for the time interval, $\Delta t$, operating the process using the desired value, $X_d$, determined in step (c) for the control signal;

(e) determining a value, $X_a$, of the control signal actually used by the actuator during the time interval, $\Delta t$;

(f) using the model, determining a computed value for the output, $O_c$, as a function of the value of the control signal determined in step (e); and (g) reiteratively repeating steps (b) through (f), each successive iteration using values for the state variables in the model that depend on the computed value of the output determined in step (f) of the previous iteration, so that control of the process tracks changes in the specified output and the process quickly converges on the specified output.

2. The method of claim 1, wherein the step of interpolating comprises the steps of:

(a) determining the difference between the second and first control signals, $X_2 - X_1$;

(b) determining the difference between the second and first corresponding output values, $O_2 - O_1$;

(c) determining a slope of a line through a data pair $(O_1, X_1)$ and a data pair $(O_2, X_2)$, from the relationship:

$$\text{slope} = (O_2 - O_1)/(X_2 - X_1); \text{ and}$$

(d) determining the desired control signal, $X_d$, as a function of the specified output, $O_s$, from the relationship:

$X_d = (O_s - (O_1 - slope*X_1))/slope$.

3. The method of claim 1, wherein the process includes constraints on the values of the control signal that can be used by the actuator, and wherein the step of operating the process for the predetermined time interval includes the step of using a value for the control signal that approximates the desired value of the control signal as closely as the constraints allow.

4. The method of claim 3, wherein the constraints comprise limits on the maximum and minimum values of the control signal.

5. The method of claim 3, wherein the constraints comprise limits on the usable resolution for the values of the signal parameters.

6. The method of claim 3, wherein the actual control signal used may be substantially unequal to the desired control signal $X_d$ for one or more time intervals due to an actuator fault, said step of determining the control signal actually used by the actuator including the step of computing a change in the output during a total accumulated time that the actuator fault continues, so that upon correction of the actuator fault, the step of determining the desired value of the control signal compensates for the total time in which the actuator was not responding to the desired control signal.

7. The method of claim 1, wherein the model is linear with respect to successive data pairs, each data pair comprising a control signal and a corresponding process output.

8. The method of claim 1, wherein the time interval is of a predetermined length unless an event is detected that alters the operation of the process or the specified output, causing the time interval to terminate prematurely.

9. A method for controlling the concentration of a drug administered intravenously at a controlled rate to a recipient to achieve a specified plasma drug concentration, wherein a linear pharmacokinetic model is used that predicts the plasma drug concentration as a function of the rate administered and as a function of a plurality of state variables and other parameters that define the current concentration of the drug in the recipient's body, said method comprising the steps of:

(a) arbitrarily selecting a first and a second rate for administering the drug during an interval of time;

(b) using the model, determining a first and a second plasma drug concentration corresponding respectively to the first and second rates, if said rates were used during the interval of time;

(c) from the first and second rates and the first and second plasma drug concentrations, determining an interpolated drug delivery rate that should produce the specified plasma drug concentration of the drug in the recipient at the end of the interval of time;

(d) delivering the drug to the recipient nominally at the interpolated rate for the interval of time;

(e) determining an actual rate at which the drug is being delivered to the recipient;

(f) using the model, determining a computed plasma drug concentration that corresponds to the actual rate and setting the plurality of state variables as a function of the computed plasma drug concentration; and (g) reiteratively repeating steps (b) through (f) for successive intervals of time, each iteration determining the interpolated rate using the model, wherein the plurality of state variables for that iteration depend on the computed plasma drug concentration from the previous iteration, thus compensating for any substantial variation between the interpolated rate of delivery and the actual rate, whereby the rate of delivery of the drug is controlled so that the specified plasma drug concentration is rapidly achieved.

10. The method of claim 9, wherein the drug is delivered to the recipient by an infusion device, said infustion device being operable to deliver the drug only at specific incremental rates, said step of delivering the drug at the interpolated rate comprising the step of delivering the drug at one of the specific incremental rates that is closest to the interpolated rate.

11. The method of claim 10, wherein the step of determining the actual rate includes the step of determining said one specific incremental rate used to deliver the drug.

12. The method of claim 10, wherein the step of determining the actual rate includes the step of determining if the drug was not delivered to the recipient by detecting a fault in the infusion device.

13. The method of claim 10, wherein the step of determining the actual rate includes the step of determining if the drug was not delivered to the recipient by detecting an occlusion in a line through which the drug is delivered to the recipient from the infusion device.

14. The method of claim 13, wherein the step of determining the interpolated rate compensates for non-delivery of the drug to the recipient for successive intervals of time, when delivery of the drug is again resumed, because the plurality of state variables changes as the computed plasma drug concentration changes during the time that the drug is not delivered to the recipient.

15. The method of claim 9, wherein the interval of time is of a predetermined duration, subject to a premature termination in response to the occurrence of a specified event affecting the actual drug delivery rate.

16. Apparatus for controlling a process to obtain a specified output, $O_s$, where the process is described by a model that defines an output of the process as a function of a specified control signal and wherein the process is affected by an actuator in response to the control signal, said apparatus comprising:

(a) processor means for:
  (i) arbitrarily selecting a first value, $X_1$, and a second value, $X_2$, for the control signal that could be applied to control the actuator for a time interval, $\Delta t$;
  (ii) initializing a plurality of state variables used in the model;
  (iii) as a function of the first and second values of the control signal, which are input to the model, respectively determining first and second output values, $O_1$ and $O_2$; and
  (iv) interpolating with respect to the first and second values of the control signal and corresponding first and second output values to determine a desired value, $X_d$, for the control signal that should produce the specified output at the end of the time interval;

(b) means for determining successive time intervals and producing time signals indicative of each of said time intervals;

(c) said processor means being connected to receive said time signals and being further operative to operate the process using a closest available control signal to the desired value $X_d$; and (d) means for determining an actual value of the control signal implemented during operation of the actuator during the interval of time; said processor means being further operative to determine a computed value, $O_c$, for the output of the process as a function of the actual value, $X_a$, of the control signal, and to repetitively and reiteratively determine the desired value, $X_d$, for successive intervals of time, using values for the plurality of state variables in the model that depend on the computed value of the output determined in a preceding iteration, so that the process rapidly converges on the specified output.

17. The apparatus of claim 16, wherein the processor means comprise a microprocessor and a nonvolatile electronic memory in which is stored a program directing the operation of the microprocessor.

18. The apparatus of claim 16, wherein the means for determining an actual value of the control signal comprise means for determining that the actuator was interrupted during one or more of the time intervals, preventing the specified value of the output from being realized.

19. The apparatus of claim 16, wherein the process or means interpolate by:
(a) determining the difference between the second and first control signals, $X_2 - X_1$;
(b) determining the difference between the second and first corresponding output values, $O_2 - O_1$;
(c) determining the slope of a line through a data pair $(O_1, X_1)$ and a data pair $(O_2, X_2)$, from the relationship:

$$\text{slope} = (O_2 - O_1)/(X_2 - X_1); \text{ and}$$

(d) determining the desired control signal, $X_d$, as a function of the specified output, $O_s$, from the relationship:

$$X_d = (O_s - (O_1 - \text{slope} \cdot X_1))/\text{slope}.$$

20. Apparatus for controlling the intravenous administration of a drug to a recipient at a controlled rate to achieve a specified plasma drug concentration, wherein a linear model is used that determines the plasma drug concentration as a function of the rate at which it is administered and as a function of a plurality of state variables and other parameters that define the current concentration of the drug in the recipient's body, said apparatus comprising:

(a) processor means, for:
(i) selecting a first and a second arbitrary rate for administering the drug during a time interval $\Delta t$;
(ii) using the model, determining a first and a second plasma drug concentration that corresponds to the first and second arbitrary rates for administering the drug; and
(iii) based on the first and second arbitrary rates and corresponding first and second plasma drug concentrations, determining an interpolated drug delivery rate that should produce the specified plasma drug concentration of the drug in the recipient at the end of the time interval;

(b) infusion means, connected to the processor means, for delivering the drug to the recipient nominally at the interpolated rate;

(c) timer means for determining successive intervals of time, said timer means producing time signals that indicate the duration of each time interval; and (d) means for determining an actual rate at which the drug is administered to the recipient by the infusion means; said processor means being further operative to apply the model to determine a computed plasma drug concentration that corresponds to the actual rate during a current time interval, where the plurality of state variables used in the model vary as a function of the computed plasma drug concentration from prior time intervals, and being still further operative to determine an interpolated drug delivery rate and a computed plasma drug concentration using the model, for successive intervals of time, and thereby controlling the infusion means to operate substantially at the interpolated drug delivery rate so that the computed blood plasma concentration rapidly approaches the specified plasma drug concentration.

21. The apparatus of claim 20, wherein the means for determining the actual rate at which the drug is administered comprise an occlusion detector to detect if an occlusion of a delivery line connecting the infusion means to the recipient has prevented the drug from being delivered to the recipient.

22. The apparatus of claim 20, wherein the means for determining the actual rate at which the drug is administered comprise a fault detector that can detect a failure in the infusion means, which prevents the drug from being delivered to the recipient.

* * * * *